(12) United States Patent
Fischer et al.

(10) Patent No.: US 10,507,125 B2
(45) Date of Patent: Dec. 17, 2019

(54) STENT

(71) Applicant: Medfirst AG, Balzers (LI)

(72) Inventors: Harald Fischer, Weingarten (DE);
Ernst Nennig, Karlsruhe (DE)

(73) Assignee: Medfirst AG, Balzers (LI)

(*) Notice: Subject to any disclaimer, the term of this patent is extended or adjusted under 35 U.S.C. 154(b) by 69 days.

(21) Appl. No.: 15/746,652

(22) PCT Filed: Jul. 23, 2015

(86) PCT No.: PCT/EP2015/066895
§ 371 (c)(1),
(2) Date: Jan. 22, 2018

(87) PCT Pub. No.: WO2017/012673
PCT Pub. Date: Jan. 26, 2017

(65) Prior Publication Data
US 2018/0221181 A1    Aug. 9, 2018

(51) Int. Cl.
*A61F 2/915* (2013.01)

(52) U.S. Cl.
CPC .... *A61F 2/915* (2013.01); *A61F 2002/91525* (2013.01); *A61F 2002/91575* (2013.01);
(Continued)

(58) Field of Classification Search
CPC ............ A61F 2/915; A61F 2002/91525; A61F 2002/91575; A61F 2002/91583;
(Continued)

(56) References Cited

U.S. PATENT DOCUMENTS

| 2004/0034402 A1 | 2/2004 | Bales et al. |
| 2004/0044401 A1 | 3/2004 | Bales et al. |

(Continued)

FOREIGN PATENT DOCUMENTS

| EP | 2 561 837 A1 | 2/2013 |
| EP | 2 594 232 A1 | 5/2013 |

(Continued)

OTHER PUBLICATIONS

International Search Report dated Jun. 14, 2016 in corresponding related International Application No. PCT/EP2015/066895 (10 pages).
(Continued)

*Primary Examiner* — Christopher D. Prone
*Assistant Examiner* — Tiffany P Shipmon
(74) *Attorney, Agent, or Firm* — Kilpatrick Townsend & Stockton LLP

(57) ABSTRACT

The invention relates to a stent for transluminal implantation in hollow organs, in particular in blood vessels, ureters, esophagi, colons, duodena, or bile ducts, comprising a substantially tubular body, which can be transferred from a compressed state having a first cross-sectional diameter into an expanded state having an enlarged second cross-sectional diameter, wherein the stent comprises a plurality of cells, which are defined by bordering elements formed by the tubular body. The stent is distinguished in that some of the cells are extended in the longitudinal direction of the stent in comparison with the remaining cells in order to form a slanted end face of the stent.

8 Claims, 2 Drawing Sheets

Figure 3:
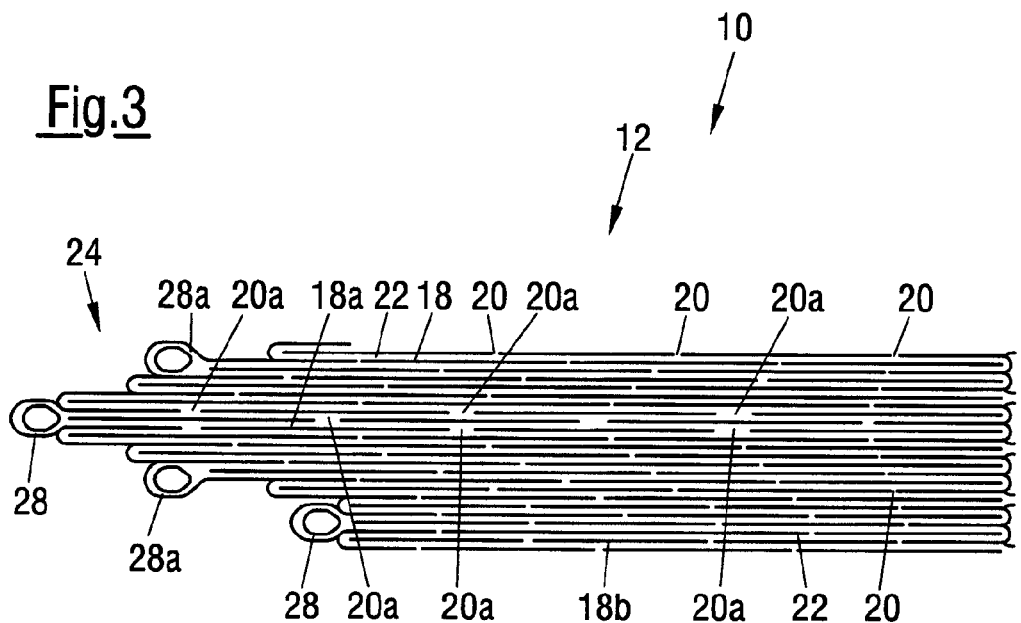

(52) U.S. Cl.
CPC .......... *A61F 2002/91583* (2013.01); *A61F 2230/0026* (2013.01); *A61F 2240/001* (2013.01); *A61F 2250/0037* (2013.01); *A61F 2250/0098* (2013.01)

(58) Field of Classification Search
CPC ........ A61F 2230/0026; A61F 2240/001; A61F 2250/0037; A61F 2250/0098
See application file for complete search history.

(56) References Cited

U.S. PATENT DOCUMENTS

| | | |
|---|---|---|
| 2010/0152835 A1 | 6/2010 | Orr |
| 2012/0245671 A1* | 9/2012 | Wainwright ............ A61F 2/915 623/1.11 |
| 2014/0277377 A1 | 9/2014 | Ischinger et al. |

FOREIGN PATENT DOCUMENTS

| | | |
|---|---|---|
| JP | 2007-090074 A | 4/2007 |
| JP | 2017-531601 A | 11/2007 |
| JP | 2010-233933 A | 10/2010 |
| JP | 5695259 B1 | 2/2015 |
| WO | 2012/008579 A1 | 1/2012 |
| WO | 2014/205124 A1 | 12/2014 |

OTHER PUBLICATIONS

Examination report in related Japanese Patent Application No. 2018-522848 dated Mar. 19, 2019 (seven pages).

* cited by examiner

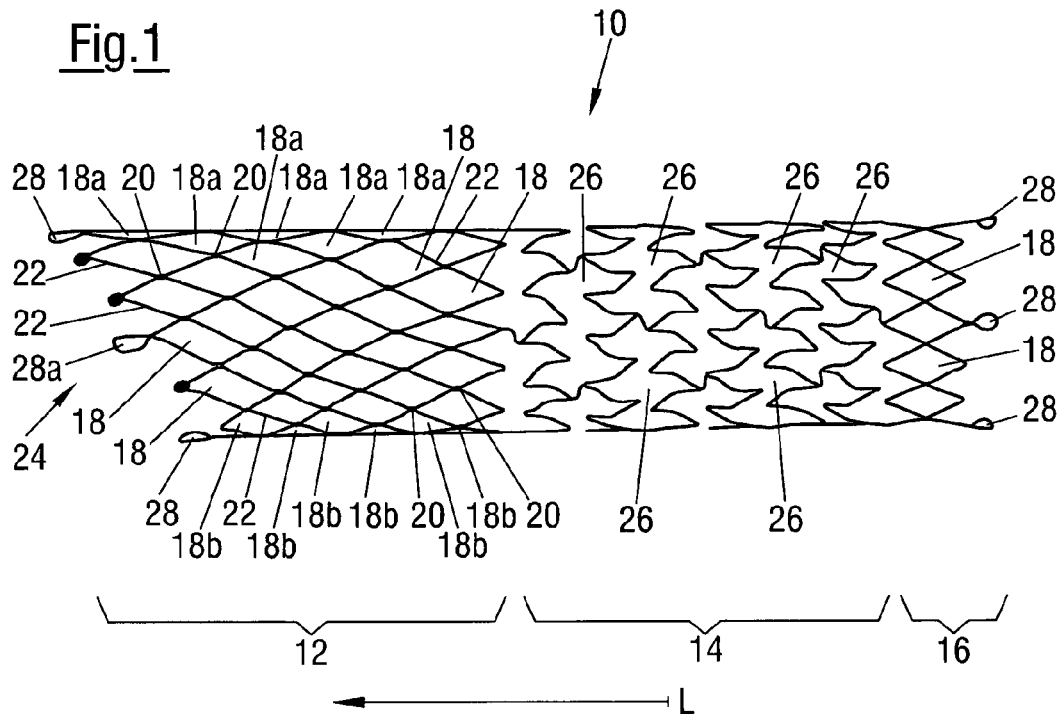
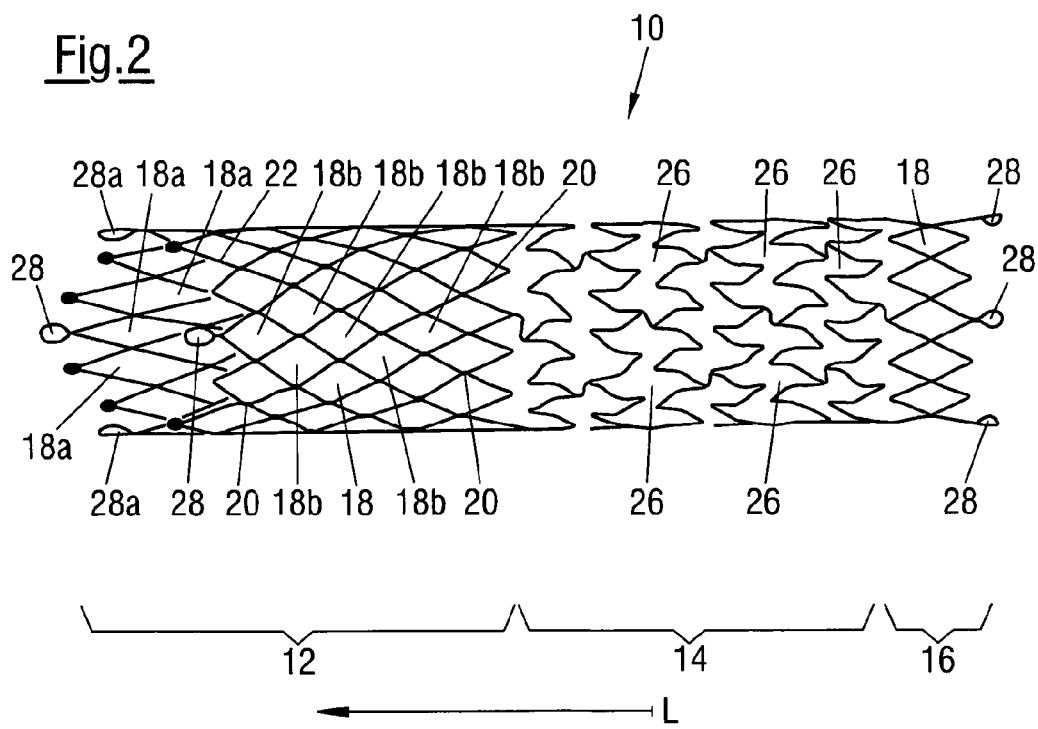

STENT

This application is a U.S. National Phase Application of PCT/EP2015/066895, filed Jul. 23, 2015, the entirety of which is incorporated by reference herein.

The present invention relates to a stent for transluminal implantation into hollow organs, in particular into blood vessels, ureters, esophagi, the colon, the duodenum or the biliary tract, having a substantially tubular body which can be converted from a compressed state having a first cross-sectional diameter into an expanded state having an enlarged second cross-sectional diameter, wherein the stent comprises a plurality of cells which are defined by bordering elements formed by the tubular body.

Stents of this type are used for the recanalization of pathologically altered hollow organs. In this respect, the stents are introduced in the compressed state via a delivery catheter to the position within the hollow organ to be treated where they are expanded by different measures to a diameter which corresponds to the diameter of the healthy hollow organ so that a supporting effect of the hollow organ, for example of a vessel wall, is achieved.

Such stents can, for example, be produced in that openings such as slits are cut into the wall of a tubular body and extend partly in the longitudinal direction of the stent so that diamond-shaped openings, for example, are produced on the expansion of the stent. An opening together with its bordering elements is called a cell.

If stents are inserted in proximity to a bifurcation of a hollow organ, stents can be used that have a chamfered end. Such vents provide the possibility of e.g. supporting a vein at all sides up to the bifurcation, i.e. for example, up to the opening into a further vein.

To be able to ensure their support effect, the stents must be able to exert a sufficient radial alignment force which counteracts a radial force effect exerted by the vessel wall. This particularly applies in the region of the chamfered end since the radial placement force is typically reduced there.

It is therefore the object of the present invention to provide a stent of the initially named kind that also provides a high radial placement force in a chamfered region, whereby a kinking of the stet on its deployment is reliably precluded.

This object is satisfied in accordance with the invention by a stent having the features of claim 1 and in particular in that some of the cells are formed in elongated form in comparison with the other cells in the longitudinal direction of the stent to form a chamfered front face end of the stent.

A chamfered end can be produced due to the elongated cells. In this respect, due to the cells elongated in the longitudinal direction, no additional cells are required to form the chamfered end. It is made possible by means of the elongated cells also to select a similar arrangement of the cells in the chamfered region as in the other tubular body.

The elongated cells can in particular only be present in a rigid section of the stent. In addition, the stent can e.g. comprise a flexible section and/or an anchorage section. The following statements with respect to the elongated cells relate to the rigid section.

A structure of the stent that can provide a particularly high radial placement force results due to the avoidance of additional cells. It is made possible in this manner to reliably support blood vessels, for example, in proximity to bifurcations. A stent in accordance with the invention can therefore be inserted, for example in the event of venous obstructions in the region of the bifurcation, the confluence of the venae iliaca communis, into the vena cava inferior, in the upper region of the vena iliaca communis. The stent can have a diameter of greater than or equal to 12 mm for this purpose. The stent can preferably have a diameter between 12 mm and 18 mm.

The dispensing with of additional cells furthermore allows the angle of the chamfer to be fixed variably since this angle can be fixed by the relative elongation of the elongated cells.

The chamfered region generally allows a reliable support of the hollow organ up to the bifurcation without, however, e.g. substantially projecting into the blood vessel after the bifurcation.

A cell can be connected to one or more other cells by a connection section or by a plurality of connection sections. The length of a cell can be understood as the spacing in the longitudinal direction between two connection sections, with the respective center of the respective connection section having to be taken into account. A cell comprises said cut-out as well as its respective bordering elements, with the connection sections belonging to the bordering elements.

In a stent in accordance with the invention, at least some of the dells can be respectively connected to one another by means of a plurality of connection sections. Three or four respective connection sections can in particular be provided in the chamfered region and/or with the elongated cells. The supporting effect can thus be particularly high due to the radial placement force that can be achieved in this manner.

The stent can be produced from a memory metal that adopts a stored shape from a limit temperature onward.

Preferred embodiments of the invention can be seen from the description, from the dependent claims and from the drawings.

In accordance with a first advantageous embodiment, at least some of the elongated cells are arranged along a straight line or an approximately straight line that in particular extends in parallel or approximately in parallel with the longitudinal direction. This means that, for example, at least one or two cells arranged after one another on the straight line can be provided. With more than two cells, at least two connection sections of at least one of these cells can be directly connected to two further ones of the elongated cells. Two respective connection sections of the elongated cells in particular lie on the straight line.

In accordance with a further advantageous embodiment, the elongated cells are divisible into a plurality of groups, in particular into nine groups, with the cells of each group being respectively arranged along a straight line or an approximately straight line and with these lines in particular extending in parallel or approximately in parallel with the longitudinal direction. Twelve groups of cells can be provided overall of which nine groups have elongated cells. With such a definition of groups, the intermediate spaces between the groups can themselves also form cells.

The arrangement of the cells can therefore be selected such that the respective cells are arranged along straight lines or approximately straight lines. In addition, the cells can be formed symmetrically to one of these lines. There can therefore in particular be no cells present that are inclined or rotated with respect to the other cells. A weakening of the structure by such rotated cells can be avoided in this manner.

All the cells within a group can in particular each have the same length or approximately the same length viewed in the longitudinal direction. Alternatively, cells having different lengths can also be provided in a group.

The lines that are formed by the cells of different groups preferably extend in parallel or approximately in parallel with one another.

A respective equal amount of cells are further preferably provided in each group from a cross-sectional plane extending perpendicular to the longitudinal axis up to the chamfered front face end. A radial placement force can be effected by the provision of a respective equal number of cells in a group that is substantially constant over the length of the stent. The same number of cells can preferably be provided in each group in the rigid section of the stent.

Respective angles that can be recognized in the so-called flat projection of the stent can in particular be formed by the connection sections of the cells on the use of an equal number of cells. The angles are defined by the peripheral direction (that is a straight line in the flat projection) and by a straight line, with the straight line extending through connection sections of the cells. This means that the connection sections of at least some of the respective cells lie on straight lines in the flat projection. The angles can be the larger, the closer the angle is to the chamfered end of the stent, with four, five, or six angles preferably being provided.

The ends of the cells cannot form a straight line in the flat projection at the chamfered end itself, but can rather define a curve that approximates a sine curve. Such a sine curve in the flat projection results in a slanted starting cut (the chamfered region) with an exactly planar cut surface at the three-dimensional stent.

The cells can be arranged such that a first angle is in a range between 20° and 24°, a second angle is in a range between 37° and 44°, a third angle is in a range between 48° and 52°, a fourth angle is in a range between 60° and 64°, a fifth angle is in a range between 63° and 67°, and a sixth angle is in a range between 69° and 73°. The largest angle can in particular be closest to the chamfered end of the stent, whereas the smallest angle is the furthest away from the chamfered end. In addition, an angle of 0° can be provided; this means that a position at the stent is present in the flat projection at which connection sections are arranged along the peripheral direction. The angle of 0° can be provided at a transition from the rigid region to the flexible region. The cells of a group can be of different lengths to form the described angles.

It has been found for such a selection of the angles that a very stable stent can be produced in this manner that has a particularly long durability.

In accordance with a further advantageous embodiment, the length of the cells of adjacent groups falls from a maximum to a minimum in the peripheral direction. Cells having a maximum length are in particular disposed opposite cells having a minimal length with respect to a central axis of the stent. The chamfer can be produced by such an arrangement.

At least some of the cells are further preferably connected to one another by means of connection sections, with the connection sections between the elongated cells, in particular only between the longest cells, being formed as elongated. The openings of the longest cells can be shortened due to the elongated or enlarged connection sections, whereby a uniform bending open of all the cells can be achieved on the expansion of the stent. Such a uniform bending open can in turn produce a uniform distribution of the radial placement force and a particularly robust stent.

At least one marker particularly preferably extends in the longitudinal direction away from the chamfered end, in particular in the form of an eyelet, with the marker having an asymmetrical shape. A marker can be a section of the stent that has an elevated impermeability to X-rays, i.e. is particularly easily visible in an X-ray. The marker can in particular be an eyelet that is, for example, filled with or covered by tantalum. The marker can also be attached in the chamfered region due to the asymmetrical shape since the marker can extend away from the chamfer.

In other words, the marker can therefore be arranged in a region between the longest and the shortest extent of the stent in the longitudinal direction. The marker can be deigned as large enough due to the asymmetrical shape to be recognized particularly easily in the X-ray. In addition, a further marker can be provided, e.g. at the tip of the chamfer. Yet a further marker can, for example, be attached at the chamfer at a shortest point of the stent.

In accordance with a further advantageous embodiment, at least two asymmetrical markers are provided at the chamfered end, with the markers in particular being disposed opposite one another with respect to an axis of the stent. The two markers can therefore be disposed symmetrically to a plane of the stent that extends through an axis of the stent and a tip of the chamfer. The asymmetrical markers can, for example, be aligned in an X-ray due to such an arrangement. As a result, the position of the stent can be recognized particularly easily in the X-ray.

In accordance with a further advantageous embodiment, the stent comprises a flexible section that adjoins the rigid section. The flexible section is disposed opposite the chamfered end. The flexible section can have cells that have a larger area in the flat projection than cells of the rigid section. The flexible section can be more easily bendable due to the larger cells, whereby the flexible section can be adapted to the shape of extent of a hollow organ in a simple manner. The cells of the flexible sections can preferably have a tooth-like boundary.

In accordance with yet a further advantageous embodiment, the stent comprises an anchorage section that adjoins the flexible section. The cells of the anchorage section can correspond to the cells of the rigid section and can, for example, be in diamond shape. The anchorage section can have a small flexibility due to the diamond-shaped cells and can thus fix the stent at its position in the hollow organ. The anchorage section can form a straight end of the stent to which markers can be attached that extend away from an end of the stent. The markers can have the shape of eyelets and can likewise e.g. be covered by or filled with tantalum. The stent can be fixed in a delivery catheter by means of the markers of the anchorage section on the introduction of the stent into the hollow organ.

The invention furthermore relates to a method of manufacturing a stent, in which method a) the stent is cut out of a tubular material; and b) the stent is widened up to its expanded state.

The method in accordance with the invention is characterized in that c) the shape of the cells of the stent is changed and fixed in the expanded state.

The individual cells can each be shaped such that a uniform expansion behavior of the individual cells is achieved by the change of the shape of the cells. In this manner, the risk of breaking can in particular be reduced with short and medium-sized cells in the proximity of the chamfered region that typically expand asymmetrically and excessively due to an inhomogeneous force distribution on expansion.

The acute angles can, for example, be reduced or changed with diamond-shaped cells having up to four connection sections at the respective corners of the diamond such that they are smaller than 70°, preferably smaller than 60°. This has the result that the stent can better withstand larger external forces in the region of the chamfered region by a homogeneous force dissipation over the structure and the risk of a stent collapse or of a stent break is considerably reduced.

It is moreover possible by means of the method to prevent too wide an expansion of cells, whereby pre-damage to connection sections can be avoided.

In accordance with an advantageous embodiment, a core to which fastening means are attached is used for widening a core to change and to fix the shape of the cells of the stent. The expansion behavior of the individual cells can therefore be adapted by the fastening means. The shape of the cells is consequently changed with respect to the expansion on a use purely of e.g. a cylindrical core. Such a cylindrical core can also comprise a conical section that facilitates the pulling on of the stent. In addition, the expansion can take place while supplying heat.

The fastening means are particularly preferably needles or mandrels that are introduced into holes of the core. The needles or mandrels can, for example, be moved from the interior out of the core or can be plugged into the core from the outside. For this purpose, for example, an automated process can be carried out by means of robots or by means of a hydraulic system, but also a manual adaptation of the cells can be carried out.

In accordance with a further advantageous embodiment, the changed shape of the cells of the stent is permanently fixed by means of a heating process. Such a fixing is in particular of advantage on the use of memory metals that adopt the shape stored by the heating process again on an increase in temperature. A permanent fixing is to be understood as a fixing of the shape of the cells of the stent in the expanded state of the stent, with the shape of the cells being maintained in the expanded state even though the stent has been changed into the compressed state in the interim. On the introduction of the stent into the body, the stent and its cells can, due to body heat, again adopt the shape taught during the manufacturing process.

The invention will be described in the following with reference to advantageous embodiments and to the enclosed drawings. There are shown:

FIG. 1 a stent in accordance with the invention in the expanded state in a side view;

FIG. 2 the stent of FIG. 1 in the expanded state in a plan view;

FIG. 3 the stent of FIG. 1 in a cut representation projected into a plane; and

Figure 4:
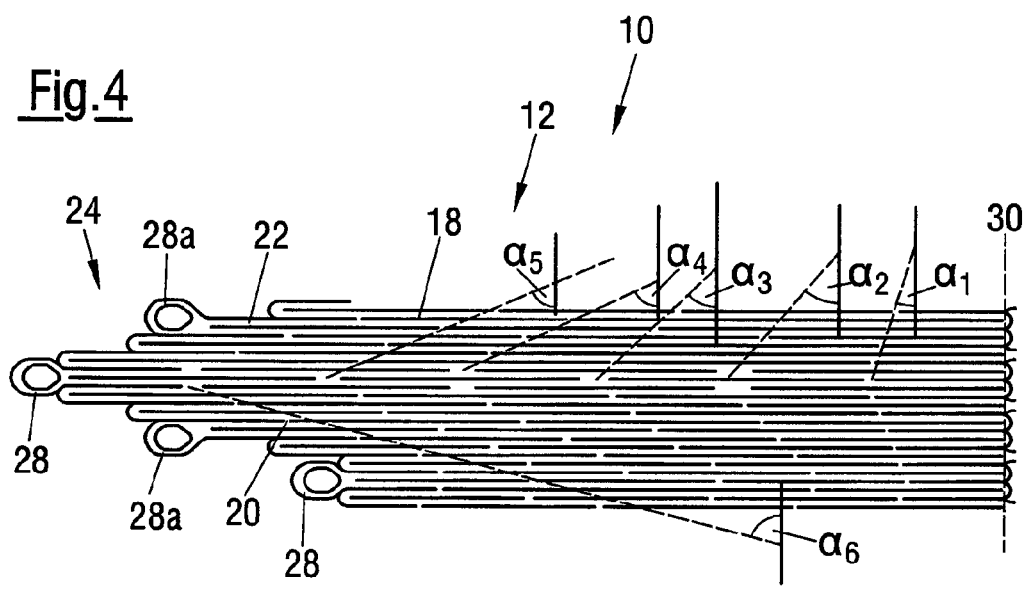

FIG. 4 a cut representation of FIG. 3 with a representation of angles that are defined by connection sections.

FIG. 1 and FIG. 2 show a stent 10. The stent 10 has a tubular design and comprises a rigid section 12, a flexible section 14 adjoining the rigid section 12, and an anchorage section 16 adjoining the flexible section 14.

The rigid section 12 is formed from diamond-shaped (closed) cells 18 that are each connected to other diamond-shaped cells 18 via three or four connection sections 20. The diamond-shaped cells 18 are defined by web-like bordering elements 22 that are shaped from a metal.

The rigid section 12 comprises a chamfered region 24 that enables the use of the stent 10 at a bifurcation (not shown) of a hollow organ.

The chamfered region 24 forms an end of the stent 10 and is produced in that some of the diamond-shaped cells 18 are formed as elongated in a longitudinal direction L. The longest diamond-shaped cells 18 are marked by reference numeral 18a in the Figures, whereas the shortest diamond-shaped cells 18 are marked by reference numeral 18b. Three of the shortest diamond-shaped cells 18b and three of the longest diamond-shaped cells 18a are respectively provided in the longitudinal direction L in the rigid section 12. The longest diamond-shaped cells 18 are in this respect disposed opposite the short diamond-shaped cells 18b with respect to a central axis of the stent 10. Three respective groups of the longest and shortest diamond-shaped cells 18a, 18b are provided next to one another (i.e. adjacent in the peripheral direction).

Open cells 26 having a serrated or tooth-like outline are arranged in the flexible section 14, with respectively fewer open serrated cells 25 being provided, viewed in the peripheral direction of the stent 10, as diamond-shaped cells 18. The flexible section is more easily deformable with respect to the longitudinal direction L due to the use of fewer open serrated cells 26 and can thus adapt easily to the extent of a blood vessel or similar.

The anchorage section 16 is formed by diamond-shaped cells 18 that provide an increased stiffness of the anchorage section 16, whereby the stent 10 reliably maintains its position in a hollow organ.

Four respective eyelet-shaped markers 28, of which a respective three are visible in FIG. 1, are provided both at the chamfered region 24 and at the end of the stent 10 formed by the anchorage section. All four markers 28 of the chamfered region 24 can be recognized in FIG. 2.

Two of the markers 28 that are attached to the points of the longest and shortest extents of the stent 10 in the chamfered region 24 are formed as symmetrical. Two further markers 28 are attached to the chamfered region 24 where the stent 10 has its average length. These two markers 28 are formed as asymmetrical marks 28a, with the area of the asymmetrical markers 28a extending toward the shortest extent of the stent.

FIG. 3 shows the rigid section 12 of the stent 10 of FIG. 1 and FIG. 2 in a so-called cut representation. FIG. 3 consequently shows a projection of cuts in a plane that are introduced into a raw material of the stent. A line thus indicates a cut. A plurality of straight cuts extending offset from one another and in parallel can be widened on the expansion of the stent 10 to form the diamond-shaped cells 18 shown in FIG. 1 and FIG. 2.

The material regions shown as white regions and present between the lines become connection sections 20 or bordering sections 22 after the expansion. FIG. 3 only shows the rigid section 12 of the stent 10.

It can be recognized in FIG. 3 that extended connection sections 20a are provided between the longest diamond-shaped cells 18a and produce a more uniform bending open of all the diamond-shaped cells 18 on the expansion of the stent.

FIG. 4 shows the view of FIG. 3 with entered angles that are formed by connection sections 20 having a peripheral direction. Six angles $\alpha_1$, $\alpha_2$, $\alpha_3$, $\alpha_4$, $\alpha_5$, $\alpha_6$ are shown that continuously increase from an angle of approximately 22° ($\alpha_1$) over angles of approximately 40° ($\alpha_2$), 50° ($\alpha_3$), 62° ($\alpha_4$), and 65° ($\alpha_5$) up to an angle of approximately 71° ($\alpha_6$). A straight end line 30 that is arranged at the transition from the rigid region 12 to the flexible region 14 extends in the peripheral direction through connection sections 20 and thus defines an angle of 0°.

REFERENCE NUMERAL LIST 10 stent
12 rigid section 14 flexible section
16 anchorage section
18, 18a, 18b diamond-shaped cell
20, 20a connection section
22 bordering element
24 chamfered region
26 open serrated cell
28, 28a markers
30 end line
L longitudinal direction
α angle

The invention claimed is:

1. A stent for transluminal implantation into hollow organs, the stent comprising:
　a substantially tubular body extending in a longitudinal direction, wherein the substantially tubular body is configured to be converted from a compressed state having a first cross-sectional diameter into an expanded state having an enlarged second cross-sectional diameter,
　wherein the stent comprises a plurality of groups of cells in the expanded state,
　wherein each group of cells comprises an equal number of cells,
　wherein each group of cells comprises three or more diamond-shaped cells that are defined by bordering elements formed by the tubular body and defined by connection sections at locations where the bordering elements intersect,
　wherein adjacent diamond-shaped cells of each group of cells are connected by one of the connection sections,
　wherein each group of cells is arranged so that the connection sections connecting adjacent diamond-shaped cells in each group of cells are oriented in a straight line that is parallel to the longitudinal direction,
　wherein diamond-shaped cells of a first group of the plurality of groups of cells are more elongated in the longitudinal direction than diamond-shaped cells of a second group of the plurality of groups of cells in order to form a chamfered front face end of the stent.

2. The stent in accordance with claim 1,
wherein the hollow organs are selected from a group of members consisting of blood vessels, ureters, esophagi, colons, duodenums and biliary tracts.

3. The stent in accordance with claim 1,
wherein a length of cells of adjacent groups of cells decreases from a maximum to a minimum in a peripheral direction.

4. The stent in accordance with claim 1,
wherein cells, in the plurality of groups of cells, having a maximum length are disposed opposite cells, in the plurality of groups of cells, having a minimum length with respect to a central axis of the stent.

5. The stent in accordance with claim 1,
wherein at least one marker extends away from the chamfered front face end in the longitudinal direction, with the marker having an asymmetrical shape.

6. The stent in accordance with claim 5,
wherein the at least one marker is an eyelet.

7. The stent in accordance with claim 5,
wherein the at least one marker is arranged in a region between a longest and a shortest extent of the stent in the longitudinal direction.

8. The stent in accordance with claim 5,
Wherein the at least one marker comprises two markers provided at the chamfered front face end, wherein the two markers are disposed opposite one another with respect to an axis of the stent.

* * * * *